(12) United States Patent
Engel et al.

(10) Patent No.: US 9,879,987 B2
(45) Date of Patent: Jan. 30, 2018

(54) POSITIONING SYSTEM AND METHOD

(71) Applicant: Airbus Defence and Space GmbH, Ottobrunn (DE)

(72) Inventors: Franz Engel, Munich (DE); Christian Weimer, Ottobrunn (DE)

(73) Assignee: Airbus Defence and Space GmbH, Taufkirchen (DE)

( * ) Notice: Subject to any disclaimer, the term of this patent is extended or adjusted under 35 U.S.C. 154(b) by 123 days.

(21) Appl. No.: 14/945,126

(22) Filed: Nov. 18, 2015

(65) Prior Publication Data

US 2016/0146598 A1 May 26, 2016

(30) Foreign Application Priority Data

Nov. 21, 2014 (EP) ..................................... 14003920

(51) Int. Cl.
| | | |
|---|---|---|
| *G01N 21/00* | (2006.01) | |
| *G01B 11/27* | (2006.01) | |
| *G01P 3/68* | (2006.01) | |
| *G01S 17/46* | (2006.01) | |
| *G01S 17/50* | (2006.01) | |
| *G01B 11/14* | (2006.01) | |
| *G01N 21/95* | (2006.01) | |
| *G01B 11/00* | (2006.01) | |

(52) U.S. Cl.
CPC .......... *G01B 11/272* (2013.01); *G01B 11/002* (2013.01); *G01B 11/14* (2013.01); *G01N 21/95* (2013.01); *G01P 3/68* (2013.01); *G01S 17/46* (2013.01); *G01S 17/50* (2013.01)

(58) Field of Classification Search
CPC ..... G01B 11/002; G01B 11/27; G01B 11/272; G01B 11/14; G01N 21/95; G01P 3/68; G01S 17/46; G01S 17/50
See application file for complete search history.

(56) References Cited

U.S. PATENT DOCUMENTS 5,689,340 A * 11/1997 Young ................ G02B 27/2214
355/22
7,978,328 B2 7/2011 Engelbart et al.
(Continued)

FOREIGN PATENT DOCUMENTS

| DE | 10 2010 044175 A1 | 5/2012 |
| DE | 10 2012 111898 A1 | 6/2014 |
| DE | 10 2013 104546 A1 | 11/2014 |

OTHER PUBLICATIONS

German Search Report for Application No. EP 14 00 39 20 dated May 18, 2015.

*Primary Examiner* — Abdullahi Nur
(74) *Attorney, Agent, or Firm* — Jenkins, Wilson, Taylor & Hunt, P.A.

(57) ABSTRACT

A positioning system for detecting a spatial position of a laying head of a device for automatically laying reinforcing fiber strips in relation to a base on which the reinforcing fiber strips can be laid by the laying head includes at least two laser lines which extend substantially in parallel at a spacing A from one another and substantially transversely to a laying direction can be projected on the laid reinforcing fiber strips by at least one laser source. The elevation profiles of the projected laser lines which occur on account of an irregular surface of the laid reinforcing fiber strips are able to be recorded by a camera and supplied to an evaluation unit.

10 Claims, 3 Drawing Sheets

(56) References Cited

U.S. PATENT DOCUMENTS

| | | |
|---|---|---|
| 8,050,486 B2 | 11/2011 | Walton |
| 9,052,294 B2 | 6/2015 | Walton |
| 2013/0228285 A1 | 9/2013 | Pause et al. |

* cited by examiner

POSITIONING SYSTEM AND METHOD

CROSS-REFERENCE TO RELATED APPLICATION

This application claims priority to EP 14 003 920.7 filed Nov. 21, 2014, the entire disclosure of which is incorporated by reference herein.

TECHNICAL FIELD

The disclosure herein relates to a positioning system for detecting a spatial position of a laying head of a device for automatically laying reinforcing fiber strips in relation to a base on which the reinforcing fiber strips can be laid by the laying head. In addition, the disclosure herein relates to a method for detecting a spatial position of a laying head of a device for automatically laying reinforcing fiber strips in relation to a base on which the reinforcing fiber strips can be laid by the laying head. Moreover, the disclosure herein relates to a method for detecting laying errors of a device for automatically laying reinforcing fiber strips on a base by a laying head.

BACKGROUND

Today, carbon-fiber-reinforced plastics materials, such as CFRP, are generally used for producing components which are lightweight but at the same time have a high mechanical loading capacity. In order to efficiently manufacture CFRP components having complex geometries, in this connection inter alia the AFP (automated fiber placement) method is used. In this case, narrow strips of carbon fibers are gradually laid beside and on top of one another on a base, by a laying head, and fixed in an appropriate manner. For this purpose, the laying head can be moved for example by a handling device, in particular a robot, in a fully automated manner along pre-programmed paths in space, at a plurality of degrees of freedom. Once the generally fully automated laying process is completed, the reinforcing fiber structure thus produced is preferably infiltrated with a thermosetting plastics material and cured. Alternatively, carbon fiber strips which are pre-impregnated with a thermosetting plastics material (prepregs) can also be laid by the laying head in a fully automated manner on a base, meaning that it is not necessary to fix the position of the dried carbon fiber strips or to subsequently infiltrate the strips with thermosetting plastics material.

A detector, arranged in the laying head, is used for quality assurance, which detector detects, in parallel with the laying process, the relative position of the carbon fiber strips to one another and searches for various laying errors and/or checks adherence to predetermined requirements. Laying errors of this kind may for example be excessive spacings between the carbon fiber strips or twisting of the carbon fiber strips. The data measured by the detector are elevation profiles. Certain types of errors, however, cannot be identified on the basis of elevation profiles alone. This is the case, for example, in the event of deviations from a predetermined target component geometry. The position or the spatial location of the measured elevation profiles must therefore be determined and if necessary taken into account by combining during evaluation.

The spatial position of the laying head can be determined by external systems. Thus, for example, a robot used for moving the laying head can output the position coordinates of the laying head. The exact position of the laser sensor and thus of the laser profile can then be determined by appropriate coordinate transformations and measurements. Alternatively, a laser tracker can also be used to determine the position of the laser sensor.

However, determining the position on the basis of data from external systems such as the robot used for moving the laying head is subject to a number of problems. It may thus be necessary to agree with the manufacturer to produce a compatible interface, although this is frequently undesirable for reasons of trade secrets or fails due to technical requirements such as the available resolution and accuracy. On the other hand, using laser trackers is usually too expensive.

SUMMARY

One idea, feature and/or object of the disclosure herein is therefore firstly to provide a positioning system which makes it possible to determine the spatial position of a laying head of a device for automatically laying reinforcing fiber strips independently of other systems. In addition, another idea, feature and/or object of the disclosure herein is to provide a method for detecting a spatial position of a laying head and a method for identifying laying errors, in particular using the positioning system according to the disclosure herein.

At least two laser lines which extend substantially in parallel at a spacing from one another and substantially transversely to a laying direction can be projected on the laid reinforcing fiber strips by at least one laser source, the elevation profiles of the projected laser lines which occur on account of an irregular surface of the laid reinforcing fiber strips being able to be recorded by a camera and supplied to an evaluation unit.

As a result, at least in the case of straight displacement movements of the laying head, the position of the laying head can be detected very accurately and independently of external systems in order to reduce errors in the laying process. Carbon fiber strips are preferably used as reinforcing fiber strips.

In the case of a favorable technical development, a laser source is provided, the principal ray of which can be split using a beam splitter in order to generate at least two separate laser beams.

As a result, just one laser source is required, which leads to a reduced outlay. Alternatively, two or more laser sources or lasers could also be provided, which are independent of one another. The at least two laser beams thus generated extend at a known spacing A in parallel with one another.

In a further embodiment, the laser beams are fanned out laterally in a trapezoidal shape in order to generate the laser lines.

As a result of the fanning out, which is lateral and/or occurs transversely to the principal ray direction, the two substantially straight laser lines appear on the already laid reinforcing fiber strips or on the uncoated base.

According to a further development, the positioning system comprises at least one sensor for detecting a rotational movement of the laying head about the vertical axis thereof.

As a result, measuring errors can be prevented when the laying head does not move in a straight line in some portions. The at least one sensor can for example be a gyrocompass, a magnetic compass or an acceleration sensor.

According to a further embodiment, at least substantially straight displacement movements of the laying head in relation to the base can be detected by the positioning system.

As a result, at least the main movement direction of the laying head of an AFP device can be detected very reliably and accurately.

In a further development, the positioning system can be arranged on a side of the laying head which is oriented counter to the laying direction.

This ensures that the positioning system is always guided over reinforcing fiber strips which are already laid on the base and/or other reinforcing fiber strips and are adequately fixed in position.

A method for detecting a spatial position of a laying head of a device for automatically laying reinforcing fiber strips in relation to a base on which the reinforcing fiber strips can be laid by the laying head, comprises:

a) projecting on the laid reinforcing fiber strips, by at least one laser source, at least two laser lines which extend in parallel at a spacing from one another and substantially transversely to a laying direction;

b) recording, by a camera, in each case at least two elevation profiles of the projected laser lines occurring on account of the irregular surface of the laid reinforcing fiber strips;

c) comparing, by an evaluation unit, two elevation profiles, recorded at different points in time $t_1$, $t_2$ respectively;

d) outputting a signal when two of the elevation profiles recorded at the points in time $t_{1,2}$ are congruent; and e) repeating steps a) to d).

As a result, at least in the case of straight displacement movements, the respective positions of the laying head in the laying direction can be determined very accurately and independently of external systems such as a handling device (industrial robot), etc. used for guiding the path of the laying head. In this case, a number n of the profile congruences occurring corresponds to a displacement path which is exactly equal to n-times the spacing between the two laser lines. If no congruence between the recorded elevation profiles is found in method step b) after a specified time has elapsed, for example an error signal can be generated, which results in a significant reduction in errors in the laying process. The base lies for example in an xy-plane of a coordinate system of the device, which plane is substantially planar at least in regions, a z-axis of the coordinate system extending in parallel with a vertical axis of the laying head. The displacement movements of the laying head occur here, by way of example, substantially in parallel with the x-axis and in a straight line. The origin of the coordinate system for example can be selected as the necessary starting point for the absolute displacement measurement using the positioning system.

In a further embodiment of the method, the two elevation profiles recorded at the points in time $t_{1,2}$ respectively are obliquely compared.

As a result, as well as detecting the linear displacement path of the laying head, the movement direction thereof in relation to the base or the reinforcing fiber strips laid thereon can be determined.

In a further development of the method, the elevation profiles are recorded and compared at a sampling rate of at least 10 Hz.

As a result, a path resolution is achieved which is sufficiently high and accurate from a metrological viewpoint in relation to the movement speed of the laying head. The current speed of the laying head in relation to the base cannot be directly determined using the method. For example the speed of the laying head at the last congruence, determined by a comparison, of two elevation profiles can be used as a starting value. Changes to this starting value can then be detected for example by measuring the acceleration of the laying head using appropriate sensors and by numerically integrating the acceleration values supplied by the sensors over time by the evaluation unit. The acceleration measurement values necessary for this purpose can be recorded for example by at least one acceleration sensor integrated in the positioning system.

A method for detecting laying errors of a device for automatically laying reinforcing fiber strips on a base by a laying head comprises:

a) projecting on the laid reinforcing fiber strips, by at least one laser source, a plurality of laser lines which extend in parallel at a spacing from one another and substantially transversely to a laying direction;

b) recording in one image, by a camera, the elevation profiles of the projected laser lines occurring on account of the irregular surface of the laid reinforcing fiber strips; and c) evaluating the image using an evaluation unit in order to detect laying errors.

As a result, any reinforcing fiber strips incorrectly laid on the base or different types of laying errors in a recording region of the camera can be reliably detected using just one image recorded by the camera. Simultaneously recording a plurality of laser lines or the elevation profiles resulting therefrom makes it possible for example to clearly distinguish between a twisted reinforcing fiber strip and overlap errors or gap errors in the reinforcing strips, which errors cannot be distinguished using just one elevation profile or appear the same in the camera image. Since a recording region of the camera usually detects just a small region of the surface of the reinforcing fiber strips laid on the base, it is generally vital to repeat steps a) to c), adjusted to the current position of the laying head, so that, ideally, the entire surface of the reinforcing fiber strips laid on the base can be sampled and examined for laying errors in a full and gap-free manner. In this case, a spacing between the laser lines or the occurring elevation profiles is as small as possible in order to be able to calculate, using the evaluation unit, a three-dimensional model of the surface of the laid reinforcing fiber strips which is as close to reality as possible, for the purpose of reliable error detection.

DETAILED DESCRIPTION

Figure 1:
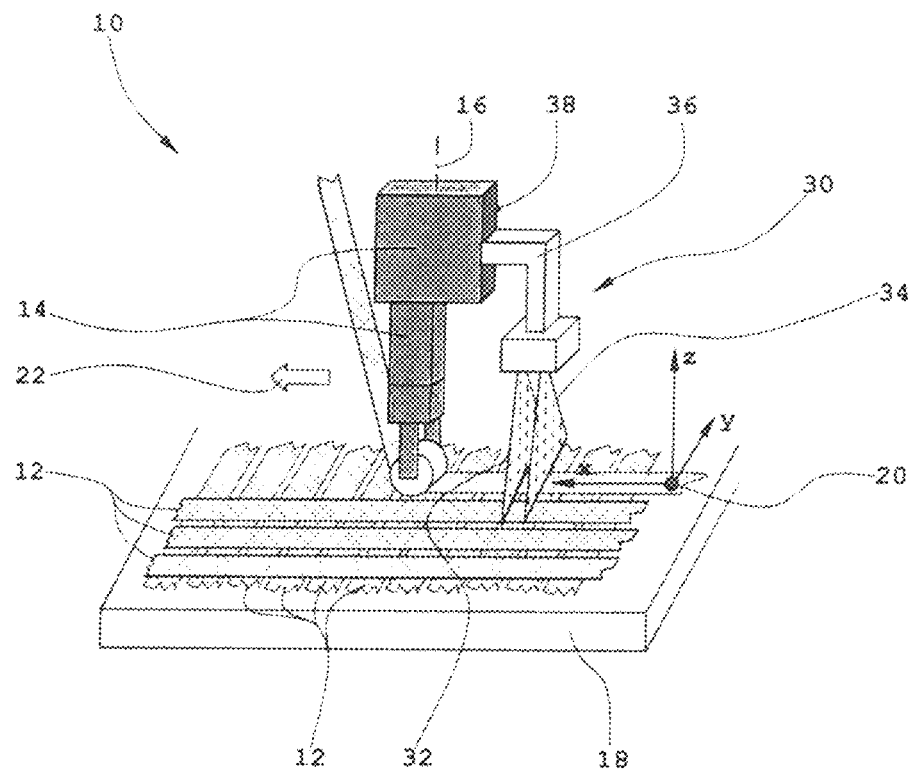
FIG. 1 is a perspective schematic view of a device for automatically laying reinforcing fiber strips on a base, comprising a positioning system according to an embodiment of the disclosure herein.

FIG. 1 is a perspective schematic view of a device for automatically laying reinforcing fiber strips on a base, comprising a positioning system according to some embodiments of the disclosure herein.

A device 10 for automatically laying reinforcing fiber strips 12 comprises a laying head 14 having a vertical axis 16. In order to gradually lay the reinforcing fiber strips 12 in layers on a base 18, the laying head 14 can be positioned by a handling device (not shown), in particular a standard industrial robot, at a plurality of degrees of freedom in relation to the base 18. For example, narrow carbon fiber strips are used as reinforcing fiber strips 12. The base 18 can have a shape which differs from the planar shape which is shown here merely by way of example, for example a surface geometry which curves in two dimensions or is convex or concave at least in regions. A z-axis of a coordinate system 20 extends in parallel with the vertical axis 16 of the laying head 14. In this case, the laying head 14 moves across the base 18 or the reinforcing fiber strips 12 already laid thereon, in a laying direction 22 in parallel with the x-axis of the coordinate system 20.

A positioning system 30 according to the disclosure herein is arranged on the laying head 14. The positioning system 30 projects a first 32 and a second 34 laser line on the base 18 or on the reinforcing fiber strips 12 laid thereon. In the case of the straight laying curve shown here, the laser lines 32, 34 extend in parallel at a spacing from one another and transversely to the laying direction 22 or to the x-axis of the coordinate system 20. The positioning system 30 is mechanically fastened on a side 38 of the laying head 14 by an appropriate support 36 which can be spatially positioned and which is oriented counter to the laying direction.

Figure 2:
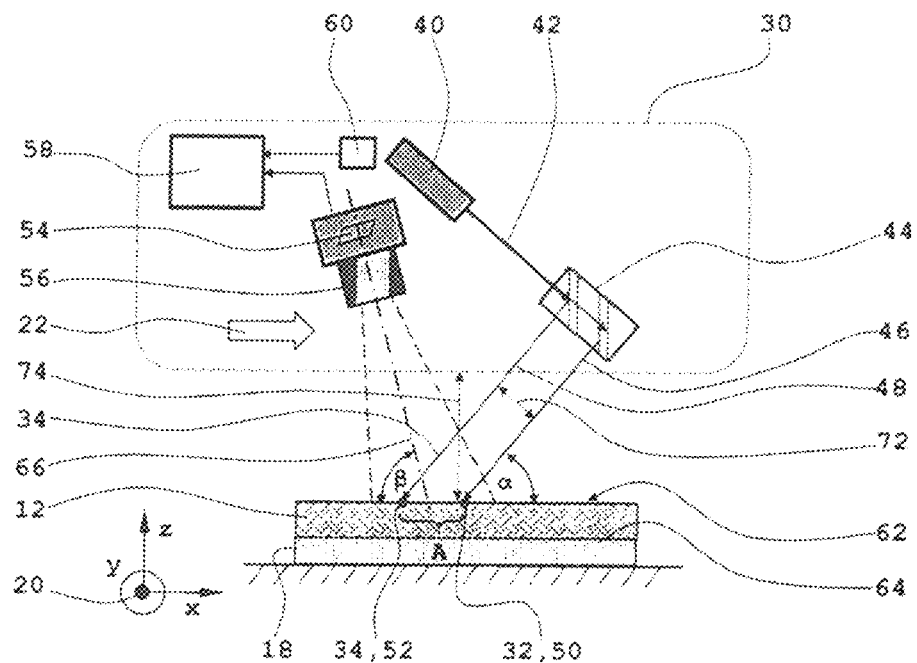
FIG. 2 is a schematic view of the positioning system of FIG. 1.

FIG. 2 is a schematic view of the positioning system of FIG. 1.

The positioning system 30 comprises inter alia a laser source 40 for generating a principal ray 42 which is split by a beam splitter 44 into a first 46 and a second 48 laser beam. The two laser beams 44, 46 are fanned out in a trapezoidal shape laterally or transversely to the laying direction (cf. FIG. 1) and are used to project the two (straight) laser lines 32, 34 on the base 18 or on the reinforcing fiber strips 12 laid thereon.

Since the surface geometry of the laid reinforcing fiber strips 12 is always different in regions, the projected laser lines 32, 34 produce a characteristic first 50 and a second elevation profile 52. An image 54 of these two elevation profiles 50, 52, shown here merely by way of example, can be recorded by a digital camera 56 and supplied to an electronic evaluation unit 58. The evaluation unit 58 may be an arithmetic unit capable of digitally evaluating images in real time, in which unit a measuring and control unit is optionally integrated. In addition, the positioning system 30 can comprise at least one sensor 60, such as an acceleration unit or a gyrocompass, for detecting location changes of the laying head about the vertical axis thereof.

There is an angle α between the two parallel laser beams 46, 48 and a surface 62 of the reinforcing fiber strips 12 or an upper side 64 of the base 18, while an optical axis 66 of the camera 56 extends at an angle β to the surface 62 or the upper side 64 of the base 18. The two laser lines 32, 34 or the elevation profiles 50, 52 in each case extend transversely to the laying direction 22 and in parallel at a spacing A from one another on the surface 62 of the reinforcing fiber strips 12. The laser lines 32, 34 may be continuously projected on the base 18 or on the reinforcing fiber strips 12 laid thereon.

The spacing A can be calculated for example from a parallel spacing 72 between the laser beams 46, 48 and is independent of a vertical elevation 74 between the positioning system 30 and the surface 62 of the reinforcing fiber strips 12 or a relative position between the positioning system 30 and the surface 62.

Figure 4:
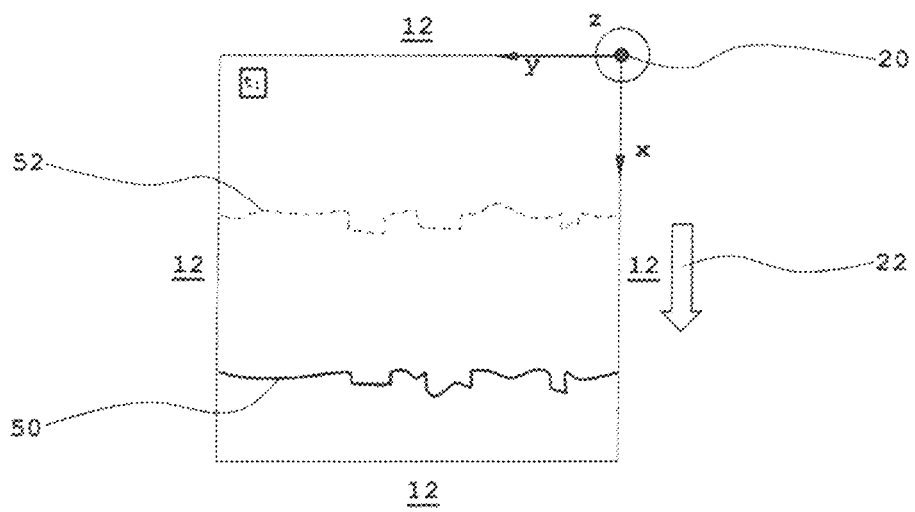
FIG. 4 shows two elevation profiles recorded at a point in time $t_1$.
Figure 5:
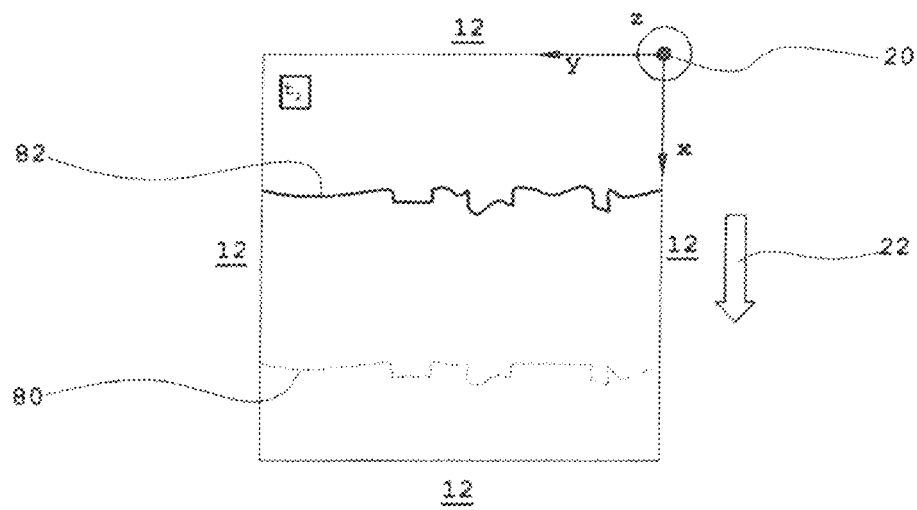
FIG. 5 shows two elevation profiles recorded at a point in time $t_2$.

The progression of the method according to some embodiments of the disclosure herein will be explained in more detail on the basis of FIG. 3, which is a plan view of laid reinforcing fiber strips having two laser lines projected thereon for generating elevation profiles, and on the basis of FIGS. 4 and 5 which schematically show two elevation profiles recorded by the camera at different points in time $t_{1,2}$ respectively.

Figure 3:
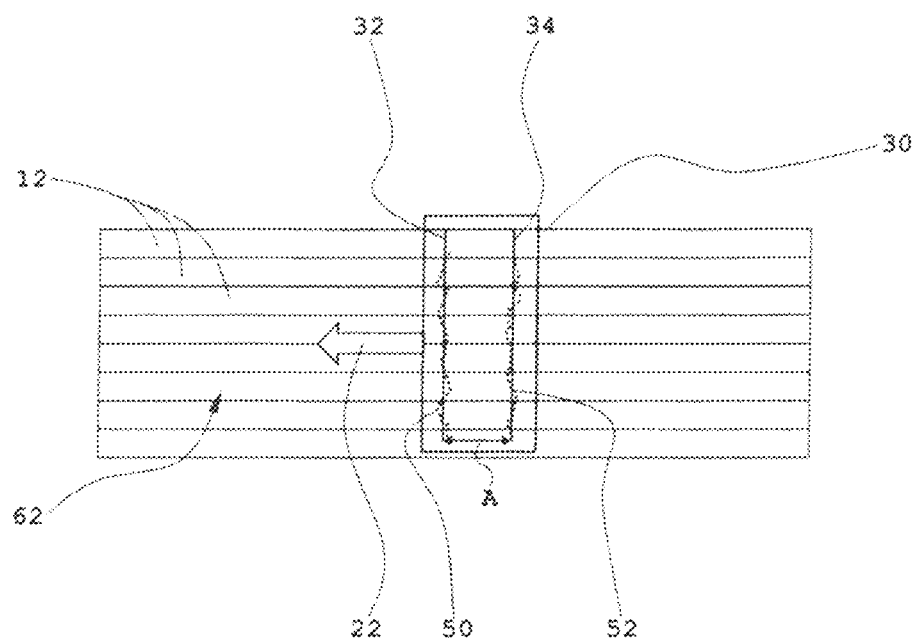
FIG. 3 is a plan view of laid reinforcing fiber strips having two laser lines projected thereon.

It can be seen from FIG. 3 that the two elevation profiles 50, 52 arise from the two projected laser lines 32, 34 on account of the surfaces 62 of the laid reinforcing fiber strips 12 which are locally always different, which elevation profiles can be recorded using the camera of the positioning system 30. If projected on a surface which is completely planar in the mathematical sense, the straight laser lines 32, 34 would likewise create straight elevation profiles 50, 52. Therefore, for proper functioning of the positioning system 30, it is assumed that the elevation profiles 50, 52 are different at each point of the laid reinforcing fiber strip 12 or of the base. On the other hand, however, use of the positioning system 30 is not provided in the case of a surface which is completely planar and/or smooth or specular in the microscopic sense.

According to the method, the elevation profiles 50, 52 occurring from the permanently projected laser lines 32, 34 are detected by the camera of the positioning system at a high frequency or sampling rate of at least 10 Hz and automatically analyzed in the evaluation unit thereof (cf. FIGS. 1 and 2). FIG. 4 schematically shows the leading first elevation profile 50 and the second elevation profile 52 lagging therebehind, which for example were recorded by the camera at the point in time $t_1$. In contrast, FIG. 5 shows a leading first elevation profile 80 and a second elevation profile 82 lagging therebehind, which profiles were both recorded at the point in time $t_2$. In this case, the laying head, together with the positioning system fastened thereto, moves across the reinforcing fiber strips 12 in the laying direction 22 or in the direction of the x-axis of the coordinate system 20. The time difference $t_2$ minus $t_1$ or a time interval $\Delta t = t_2 - t_1$ is of a size such that the elevation profiles 50, 52, 80, 82 can be continuously recorded and evaluated by the camera at an appropriate sampling rate or frequency of at least 10 Hz. According to the method, projecting the laser lines, recording the elevation profiles 50, 52, 80, 82 resulting therefrom and comparing the profiles for congruency is continuously repeated, wherein an image recording frequency or an image sampling rate of at least 10 Hz is sought.

The method steps may, in some instances, only be repeated once a delay time has elapsed, in particular in order to compensate for delays before the camera is again ready to record.

In a further method step, after the laser lines have been projected and the elevation profiles 50, 52, 80, 82 have been recorded, the actual evaluation is carried out within the evaluation unit of the positioning system by comparing for congruence the two elevation profiles 50, 52 and 80, 82 recorded at the different points in time $t_{1,2}$ respectively. If this comparison shows that two identical elevation profiles are present at the points in time $t_{1,2}$—as is the case by way of example in the elevation profiles 50 and 82 in FIGS. 4 and 5—the evaluation unit outputs an appropriate internal signal or a marker. The presence of this signal indicates that the laying head has been displaced in the laying direction, i.e. parallel to the x-axis of the coordinate system, by the spacing A between the projected laser lines or the two parallel elevation profiles 50, 52 and 80, 82 respectively, in the time interval $t_2$ minus $t_1$ or the measuring interval $\Delta t$.

Inter alia the current displacement speed v of the laying head can be calculated by the evaluation unit from the time difference $t_2-t_1$ and the spacing A. Here, by way of example, an absolute displacement path x along the x-axis of the coordinate system 20 can be calculated by the evaluation unit according to the relation x=n*A, from a number n of the signals output by the evaluation unit and based on an origin.

In addition, the movement direction of the laying head, i.e. whether the movement of the laying head is in or counter to the x-axis of the coordinate system 20, can be determined within the evaluation unit from an oblique comparison of the elevation profiles 50, 52, 80, 82. If for example, as here, the elevation profiles 50, 82 are congruent, the laying head has moved further in the laying direction 22, together with the positioning system. However, if, the opposite is the case and the elevation profile 80 and the elevation profile 52 are congruent, a movement has occurred counter to the laying direction 22 or the x-axis of the coordinate system 20.

In the method according to some embodiments of the disclosure herein for detecting laying errors using the positioning system, the simultaneous projection of a plurality of laser lines generates a plurality of elevation profiles, which can be recorded in a single image by the camera. Then the evaluation unit can use the elevation profiles to model, within the evaluation unit, a digital 3D model of at least one region of the surface of the laid reinforcing fiber strips which can be detected by the camera. As a result, various types of laying errors, such as the twisting of reinforcing fiber strips about the longitudinal axis thereof, gaps between adjacent reinforcing fiber strips or overlapping of reinforcing fiber strips can be clearly identified using appropriate image analysis algorithms.

Figure 6:
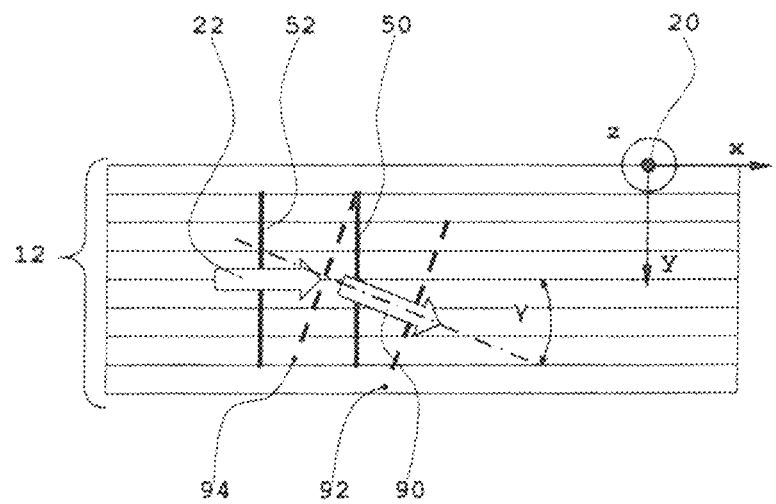
FIG. 6 is a plan view of laid reinforcing fiber strips having two pairs of parallel elevation profiles in the case of a displacement of the laying head which deviates from a straight course.

FIG. 6 is a plan view of laid reinforcing fiber strips having two pairs of parallel elevation profiles in the case of a displacement of the laying head which deviates from a straight course.

First, the laying head moves, together with the positioning system, in the laying direction 22 and the elevation profiles 50, 52 are detected. Subsequently, the laying head is pivoted through an angle γ, here by way of example approximately 22.5°, about the vertical axis thereof or the z-axis of the coordinate system 20, as a result of which two elevation profiles 90, 92 which are likewise spaced apart in parallel and likewise pivoted through the angle γ are recorded by the camera of the positioning system and supplied to the evaluation unit for further analysis.

The sensor mentioned at the outset (cf. FIG. 2), for example, can be used to detect the pivoting movements of the laying head about the vertical axis thereof, which sensor can for example take the form of an acceleration sensor, a gyrocompass or optionally also an electromagnetic compass. On the basis of the angle γ determined by the sensor, the elevation profiles 90, 92 recorded by the camera can be recombined in the evaluation unit by digital image processing algorithms and subsequently in turn compared with one another in order to determine congruences between the elevation profiles 50, 52, 90, 92 processed in this way.

The positioning system according to the disclosure herein thus makes it possible to precisely determine the location of the laying head in relation to the base or the reinforcing fiber strips laid thereon, independently of the displacement measurement system of the handling device or the standard industrial robot used for positioning the laying head.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

What is claimed is:

1. A positioning system for detecting a spatial position of a laying head of a device for automatically laying reinforcing fiber strips in relation to a base on which the reinforcing fiber strips can be laid by the laying head,
    wherein at least two laser lines which extend substantially in parallel at a spacing from one another and substantially transversely to a laying direction can be projected on laid reinforcing fiber strips by at least one laser source, elevation profiles of the projected laser lines which occur on account of an irregular surface of the laid reinforcing fiber strips being able to be recorded by a camera and supplied to an evaluation unit.

2. The positioning system according to claim 1, wherein a laser source is provided, the principal ray of which can be split using a beam splitter in order to generate at least two separate laser beams.

3. The positioning system according to claim 2, wherein the laser beams are fanned out laterally in a trapezoidal shape in order to generate the laser lines.

4. The positioning system according to claim 1, wherein the positioning system comprises at least one sensor for detecting rotational movement of the laying head about the vertical axis thereof.

5. The positioning system according to claim 1, wherein at least substantially straight displacement movements of the laying head in relation to the base can be detected by the positioning system.

6. The positioning system according to claim 1, wherein the positioning system is arranged on a side of the laying head which is oriented counter to the laying direction.

7. A method for detecting a spatial position of a laying head of a device for automatically laying reinforcing fiber strips in relation to a base on which the reinforcing fiber strips can be laid by the laying head, the method comprising:
    projecting on laid reinforcing fiber strips, by at least one laser source, at least two laser lines which extend in parallel at a spacing from one another and substantially transversely to a laying direction;
    recording, by a camera, in each case at least two elevation profiles of the projected laser lines occurring on account of an irregular surface of the laid reinforcing fiber strips;
    comparing, by an evaluation unit, two elevation profiles, recorded at different points in time t1, t2 respectively;
    outputting a signal when two of the elevation profiles recorded at the points in time t1,2 are congruent; and
    repeating the steps above.

8. The method according to claim 7, wherein the two elevation profiles recorded at the points in time $t_{1,2}$ respectively are obliquely compared.

9. The method according to claim 7, wherein the elevation profiles are recorded and compared at a sampling rate of at least 10 Hz.

10. A method for detecting laying errors of a device for automatically laying reinforcing fiber strips on a base by a laying head, the method comprising:
- projecting on laid reinforcing fiber strips, by at least one laser source, a plurality of laser lines which extend in parallel at a spacing from one another and substantially transversely to a laying direction;
- recording in one image, by a camera, elevation profiles of the projected laser lines occurring on account of an irregular surface of the laid reinforcing fiber strips; and
- evaluating the image using an evaluation unit in order to detect laying errors.

* * * * *